(12) United States Patent
Schultz

(10) Patent No.: US 8,814,897 B1
(45) Date of Patent: Aug. 26, 2014

(54) CONTAGION PREVENTION SYSTEMS

(76) Inventor: Joseph P. Schultz, Atlanta, GA (US)

( * ) Notice: Subject to any disclaimer, the term of this patent is extended or adjusted under 35 U.S.C. 154(b) by 176 days.

(21) Appl. No.: 13/180,884

(22) Filed: Jul. 12, 2011

Related U.S. Application Data

(63) Continuation-in-part of application No. 12/877,896, filed on Sep. 8, 2010, now abandoned, which is a continuation-in-part of application No. 10/123,966, filed on Apr. 16, 2002, now Pat. No. 7,802,574, which is a continuation-in-part of application No. 09/484,666, filed on Jan. 18, 2000, now abandoned.

(60) Provisional application No. 61/363,614, filed on Jul. 12, 2010, provisional application No. 61/383,666, filed on Sep. 16, 2010.

(51) Int. Cl.
*A61B 1/267* (2006.01)

(52) U.S. Cl.
USPC ........................................ 606/185; 606/186

(58) Field of Classification Search
USPC ........................................ 600/185, 186, 240
See application file for complete search history.

(56) References Cited

U.S. PATENT DOCUMENTS

| | | | |
|---|---|---|---|
| 2,549,514 A | 4/1951 | Oertel | |
| 3,537,447 A | 11/1970 | Gauthier et al. | |
| 3,545,433 A * | 12/1970 | Horn | 600/240 |
| 4,275,719 A | 6/1981 | Mayer | |
| 4,697,578 A * | 10/1987 | Burgin | 600/212 |
| 4,958,623 A | 9/1990 | Rocco | |
| 5,360,018 A | 11/1994 | Chen | |
| 5,562,686 A | 10/1996 | Sauer et al. | |
| 2002/0108614 A1 * | 8/2002 | Schultz | 128/207.14 |

* cited by examiner

*Primary Examiner* — Nicholas Woodall
(74) *Attorney, Agent, or Firm* — Gardner Groff Greenwald & Villanueva, PC

(57) ABSTRACT

Contagion prevention systems used in oral examinations.

11 Claims, 6 Drawing Sheets

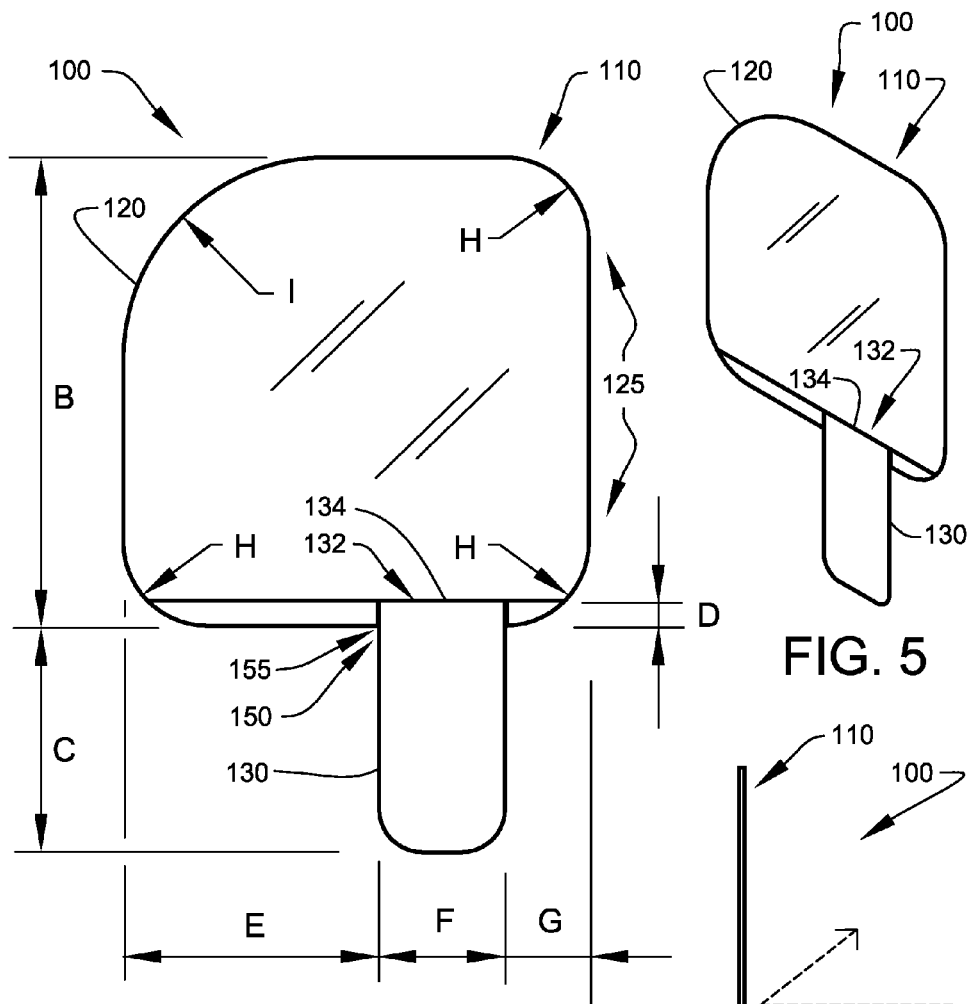
FIG. 5
FIG. 6
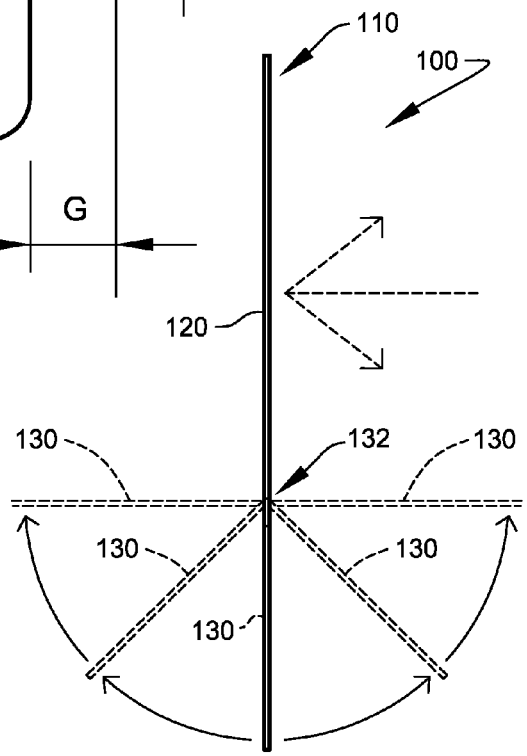
FIG. 7

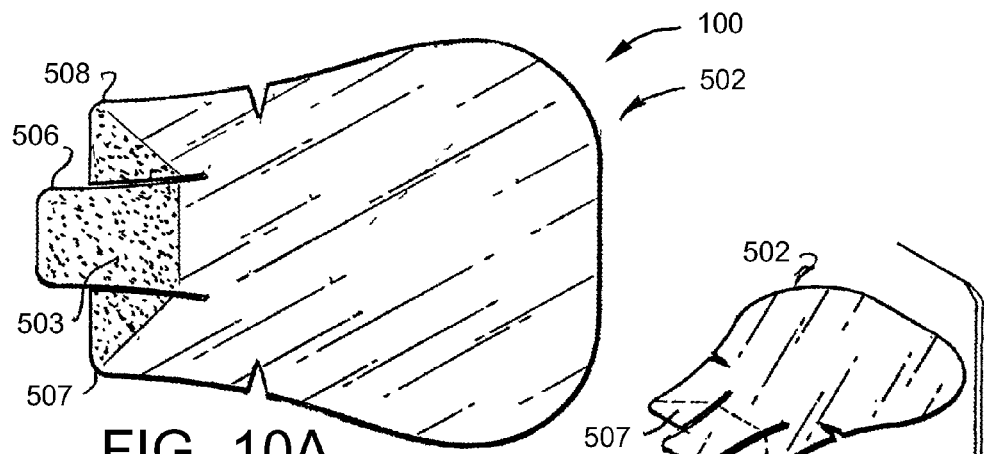
FIG. 10A
FIG. 10B
FIG. 10C
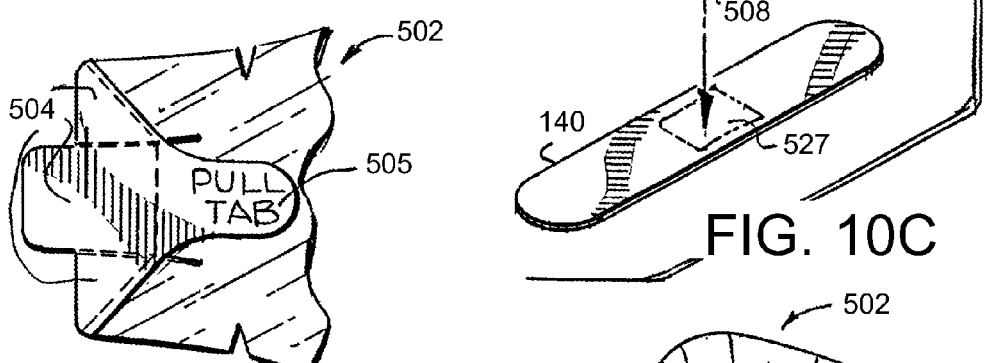
FIG. 10D
FIG. 10E
FIG. 10F

CONTAGION PREVENTION SYSTEMS

CROSS-REFERENCE TO RELATED APPLICATION

The present application is a continuation-in-part of related application Ser. No. 12/877,896, filed Sep. 8, 2010, entitled "MEDICAL COMPONENT SYSTEM", which is a continuation-in-part of related application Ser. No. 10/123,966, filed Apr. 16, 2002, entitled "MEDICAL COMPONENT SYSTEM", which is a continuation-in-part of related application Ser. No. 09/484,666, filed Jan. 18, 2000, entitled "MEDICAL COMPONENT SYSTEM"; and, this application is related to and claims priority from prior provisional application Ser. No. 61/363,614, filed Jul. 12, 2010, entitled "CONTAGION PREVENTION SYSTEMS"; and, this application is further related to and claims priority from prior provisional application Ser. No. 61/383,666, filed Sep. 16, 2010, entitled "CONTAGION PREVENTION SYSTEMS", the contents of all of which are incorporated herein by this reference and are not admitted to be prior art with respect to the present invention by the mention in this cross-reference section.

BACKGROUND

This invention relates to providing a system for improved protection from contagious diseases. More particularly this invention relates to providing a system for protection a medical practitioner during oral examination of a patient. Patients having a contagious disease may transmit that disease to the medical practitioner through body fluids expelled from the mouth, during an oral examination. The medical practitioner needs to be close to the patient to orally examine and take culture swabs from the patient's mouth and throat. It is desirable, however, to prevent potential spread of disease to the medical practitioner.

OBJECTS AND FEATURES OF THE INVENTION

A primary object and feature of the present invention is to provide a contagion prevention system overcoming the above-mentioned problem.

It is a further object and feature of the present invention to provide such a contagion prevention system placing a barrier between patient and medical practitioner.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a system comprising a cough shield capable of being held together with a tongue depressor by a single hand in a configuration usable during oral examination of a patient to assist preventing spattering of oral fluids of the patient on an examining medical practitioner. Moreover, it provides such a system further comprising a configuration selector allowing selection between left-handed and right-handed use. Additionally, it provides such a system further capable of allowing viewing through such cough shield. Also, it provides such a system further capable of allowing use of another medical instrument in a second hand without displacing such configuration which assists preventing spattering of oral fluids of the patient on an examining medical practitioner.

In accordance with another preferred embodiment hereof, this invention provides a method, relating to preventing transmission of contagion from a patient to a medical practitioner, such method comprising the steps of: providing at least one bio-matter blocker structured and arranged to assist blocking of bio-matter, potentially bearing contagion, expelled from the patient toward the face of the medical practitioner; and instructing use of bio-matter blocker in conjunction with at least one tongue depressor.

In accordance with another preferred embodiment hereof, this invention provides a system, relating to preventing transmission of contagion from a patient to a medical practitioner, such system comprising: at least one bio-matter blocker structured and arranged to assist blocking of bio-matter, potentially bearing contagion, expelled from the patient toward the face of the medical practitioner when the medical practitioner performs an examination requiring close proximity to the patient; at least one viewer structured and arranged to permit viewing of at least one portion of the patient through such at least one bio-matter blocker, when the medical practitioner performs such an examination requiring close proximity to the patient; at least one first medical-instrument passage structured and arranged to permit passage of at least one first medical instrument beyond such at least one bio-matter blocker; at least one unitary manipulator structured and arranged to permit unitary manipulation of such at least one bio-matter blocker together with such at least one first medical-instrument, when the medical practitioner performs such an examination; and at least one relative-position adjuster structured and arranged to permit adjustment of such at least one first medical-instrument relative in position to such at least one bio-matter blocker, when the medical practitioner performs such an examination; wherein potential spread of contagion from the patient to the medical practitioner is prevented, while the medical practitioner performs such an examination requiring close proximity to the patient.

In addition, it provides such a system wherein such at least one first medical-instrument passage is structured and arranged to permit passage of at least one tongue depressor beyond such at least one bio-matter blocker. And, it provides such a system wherein such at least one first medical-instrument passage is capable of mating with such at least one tongue depressor. Further, it provides such a system wherein such at least one first medical-instrument passage comprises at least one groove in such at least one bio-matter blocker. Even further, it provides such a system further comprising at least one hand-holder structured and arranged to permit hand-holding of such at least one bio-matter blocker between such at least one portion of the patient and the face of the medical practitioner, when the medical practitioner performs such an examination.

Moreover, it provides such a system further comprising at least one handed-deployment selector structured and arranged to permit selecting either right-handed or left-handed deployment of such at least one bio-matter blocker. Additionally, it provides such a system further comprising at least one second medical-instrument passage structured and arranged to permit passage of at least one second medical instrument beyond such at least one bio-matter blocker. Also, it provides such a system wherein such at least one first medical-instrument passage is structured and arranged to permit passage of at least one tongue depressor beyond such at least one bio-matter blocker. In addition, it provides such a system wherein such at least one second medical-instrument passage is structured and arranged to permit passage of at least one culture swab beyond such at least one bio-matter blocker.

And, it provides such a system further comprising at least one independent manipulator structured and arranged to permit manipulation of such at least one second medical-instrument independent from such at least one bio-matter blocker, when the medical practitioner performs such an examination. Further, it provides such a system further comprising at least one hand-holder structured and arranged to permit hand-holding of such at least one bio-matter blocker between such at least one portion of the patient and the face of the medical practitioner, when the medical practitioner performs such an examination. Even further, it provides such a system further comprising at least one handed-deployment selector structured and arranged to permit selecting either right-handed or left-handed deployment of such at least one bio-matter blocker.

In accordance with another preferred embodiment hereof, this invention provides a system, relating to preventing transmission of contagion from a patient to a medical practitioner, such system comprising: at least one bio-matter blocker structured and arranged to assist blocking of bio-matter, potentially bearing contagion, expelled from the patient toward the face of the medical practitioner, when the medical practitioner performs an examination requiring close proximity to the patient; at least one viewer structured and arranged to permit viewing of at least one portion of the patient through such at least one bio-matter blocker; and at least one hand-holder structured and arranged to permit hand-holding of such at least one bio-matter blocker between such at least one portion of the patient and the face of the medical practitioner, when the medical practitioner performs such an examination; wherein potential spread of contagion from the patient to the medical practitioner is prevented while the medical practitioner performs an examination requiring close proximity to the patient.

Moreover, it provides such a system further comprising at least one hand-holder angled-deployer structured and arranged to deploy such at least one hand-holder at at least one angle relative to such at least one viewer. Additionally, it provides such a system wherein such at least one hand-holder angled-deployer permits flat storage of such system. Also, it provides such a system further comprising at least one handed-deployment selector structured and arranged to permit selecting either right-handed or left-handed deployment of such at least one bio-matter blocker. In addition, it provides such a system further comprising at least one first medical-instrument passage structured and arranged to permit passage of at least one first medical instrument beyond such at least one bio-matter blocker.

And, it provides such a system further comprising at least one unitary manipulator structured and arranged to permit unitary manipulation of such at least one bio-matter blocker together with such at least one first medical-instrument, when the medical practitioner performs such an examination. Further, it provides such a system wherein at least one first medical-instrument passage is structured and arranged to permit passage of at least one tongue depressor beyond such at least one bio-matter blocker. Even further, it provides such a system wherein such at least one first medical-instrument passage is capable of mating with such at least one tongue depressor.

Moreover, it provides such a system wherein such at least one first medical-instrument passage comprises at least one groove in such at least one bio-matter blocker. Additionally, it provides such a system further comprising at least one relative-position adjuster structured and arranged to permit adjustment of such at least one first medical-instrument relative in position to such at least one bio-matter blocker, when the medical practitioner performs such an examination. Also, it provides such a system further comprising at least one second medical-instrument passage structured and arranged to permit passage of at least one second medical instrument beyond such at least one bio-matter blocker.

In addition, it provides such a system wherein at least one first medical-instrument passage is structured and arranged to permit passage of at least one tongue depressor beyond such at least one bio-matter blocker. And, it provides such a system wherein at least one second medical-instrument passage is structured and arranged to permit passage of at least one culture swab beyond such at least one bio-matter blocker.

Further, it provides such a system further comprising at least one independent manipulator structured and arranged to permit manipulation of such at least one second medical-instrument independent from such at least one bio-matter blocker, when the medical practitioner performs such an examination. Even further, it provides such a system further comprising at least one handed-deployment selector structured and arranged to permit selecting either right-handed or left-handed deployment of such at least one bio-matter blocker.

In accordance with another preferred embodiment hereof, this invention provides a system, relating to preventing transmission of contagion from a patient to a medical practitioner, such system comprising: at least one bio-matter blocker structured and arranged to assist blocking of bio-matter, potentially bearing contagion, expelled from the patient toward the face of the medical practitioner; at least one viewer structured and arranged to permit viewing of at least one portion of the patient through such at least one bio-matter blocker, when the medical practitioner performs an examination requiring close proximity to the patient; at least one first medical-instrument passage structured and arranged to permit passage of at least one first medical instrument beyond such at least one bio-matter blocker; at least one second medical-instrument passage structured and arranged to permit passage of at least one second medical instrument beyond such at least one bio-matter blocker; at least one unitary manipulator structured and arranged to permit unitary manipulation of such at least one bio-matter blocker together with such at least one first medical-instrument, when the medical practitioner performs such an examination; and at least one independent manipulator structured and arranged to permit manipulation of such at least one second medical-instrument independent from such at least one bio-matter blocker, when the medical practitioner performs such an examination; wherein potential spread of contagion from the patient to the medical practitioner is prevented while the medical practitioner performs an examination requiring close proximity to the patient.

Moreover, it provides such a system wherein at least one first medical-instrument passage is structured and arranged to permit passage of at least one tongue depressor beyond such at least one bio-matter blocker. Additionally, it provides such a system wherein such at least one first medical-instrument passage is capable of mating with such at least one tongue depressor. Also, it provides such a system wherein such at least one first medical-instrument passage comprises at least one groove in such at least one bio-matter blocker.

In addition, it provides such a system wherein such at least one second medical-instrument passage is structured and arranged to permit passage of at least one culture swab beyond such at least one bio-matter blocker. And, it provides such a system further comprising at least one relative-position adjuster structured and arranged to permit adjustment of such at least one first medical-instrument relative in position to such at least one bio-matter blocker, when the medical practitioner performs such an examination. Further, it provides such a system further comprising at least one handed-deployment selector structured and arranged to permit selecting either right-handed or left-handed deployment of such at least one bio-matter blocker.

Even further, it provides such a system further comprising at least one hand-holder structured and arranged to permit hand-holding of such at least one bio-matter blocker between such at least one portion of the patient and the face of the medical practitioner, when the medical practitioner performs such an examination.

In accordance with another preferred embodiment hereof, this invention provides a system, relating to preventing transmission of contagion from a patient to a medical practitioner, such system comprising: bio-matter blocker means for assisting blocking of bio-matter, potentially bearing contagion, expelled from the patient toward the face of the medical practitioner, when the medical practitioner performs an examination requiring close proximity to the patient; viewer means for permitting viewing of at least one portion of the patient through such bio-matter blocker means, when the medical practitioner performs such an examination requiring close proximity to the patient; first medical-instrument passage means for permitting passage of at least one first medical instrument beyond such bio-matter blocker means; unitary manipulator means for permitting unitary manipulation of such bio-matter blocker means together with such at least one first medical-instrument, when the medical practitioner performs such an examination; and relative-position adjuster means for permitting adjustment of such at least one first medical-instrument relative in position to such bio-matter blocker means, when the medical practitioner performs such an examination; wherein potential spread of contagion from the patient to the medical practitioner is prevented, while the medical practitioner performs such an examination requiring close proximity to the patient.

Moreover, it provides such a system further comprising hand-holder means for permitting hand-holding of such bio-matter blocker means between such at least one portion of the patient and the face of the medical practitioner, when the medical practitioner performs such an examination. Additionally, it provides such a system further comprising handed-deployment selector means for permitting selecting either right-handed or left-handed deployment of such bio-matter blocker means. Also, it provides such a system further comprising second medical-instrument passage means for permitting passage of at least one second medical instrument beyond such bio-matter blocker means.

In addition, it provides such a system further comprising independent manipulator means for permitting manipulation of such at least one second medical-instrument independent from such bio-matter blocker means, when the medical practitioner performs such an examination. And, it provides such a system further comprising hand-holder means for permitting hand-holding of such bio-matter blocker means between such at least one portion of the patient and the face of the medical practitioner, when the medical practitioner performs such an examination. Further, it provides such a system further comprising handed-deployment selector means for permitting selecting either right-handed or left-handed deployment of such bio-matter blocker means.

In accordance with another preferred embodiment hereof, this invention provides a system, relating to preventing transmission of contagion from a patient to a medical practitioner, such system comprising: bio-matter blocker means for assisting blocking of bio-matter, potentially bearing contagion, expelled from the patient toward the face of the medical practitioner, when the medical practitioner performs an examination requiring close proximity to the patient; viewer means for permitting viewing of at least one portion of the patient through such bio-matter blocker means; and hand-holder means for permitting hand-holding of such bio-matter blocker means between such at least one portion of the patient and the face of the medical practitioner, when the medical practitioner performs such an examination; wherein potential spread of contagion from the patient to the medical practitioner is prevented, while the medical practitioner performs an examination requiring close proximity to the patient.

Even further, it provides such ay system further comprising hand-holder angled-deployer means for deploying such hand-holder means at at least one angle relative to such viewer means. Moreover, it provides such a system wherein such hand-holder angled-deployer means permits flat storage of such system. Additionally, it provides such a system further comprising handed-deployment selector means for permitting selecting either right-handed or left-handed deployment of such bio-matter blocker means. Also, it provides such a system further comprising first medical-instrument passage means for permitting passage of at least one first medical instrument beyond such bio-matter blocker means.

In addition, it provides such a system further comprising unitary manipulator means for permitting unitary manipulation of such bio-matter blocker means together with such at least one first medical-instrument, when the medical practitioner performs such an examination. And, it provides such a system further comprising relative-position adjuster means for permitting adjustment of such at least one first medical-instrument relative in position to such bio-matter blocker means, when the medical practitioner performs such an examination.

Further, it provides such a system further comprising second medical-instrument passage means for permitting passage of at least one second medical instrument beyond such bio-matter blocker means. Even further, it provides such a system further comprising independent manipulator means for permitting manipulation of such at least one second medical-instrument independent from such bio-matter blocker means, when the medical practitioner performs such an examination. Even further, it provides such a system further comprising handed-deployment selector means for permitting selecting either right-handed or left-handed deployment of such bio-matter blocker means.

In accordance with another preferred embodiment hereof, this invention provides a system, relating to preventing transmission of contagion from a patient to a medical practitioner, such system comprising: bio-matter blocker means for assisting blocking of bio-matter, potentially bearing contagion, expelled from the patient toward the face of the medical practitioner; viewer means for permitting viewing of at least one portion of the patient through such bio-matter blocker means, when the medical practitioner performs an examination requiring close proximity to the patient; first medical-instrument passage means for permitting passage of at least one first medical instrument beyond such bio-matter blocker means; second medical-instrument passage means for permitting passage of at least one second medical instrument beyond such bio-matter blocker means; unitary manipulator means for permitting unitary manipulation of such bio-matter blocker means together with such at least one first medical-instrument, when the medical practitioner performs such an examination; and independent manipulator means for permitting manipulation of such at least one second medical-instrument independent from such bio-matter blocker means, when the medical practitioner performs such an examination; wherein potential spread of contagion from the patient to the medical practitioner is prevented, while the medical practitioner performs an examination requiring close proximity to the patient.

Even further, it provides such a system further comprising relative-position adjuster means for permitting adjustment of such at least one first medical-instrument relative in position to such bio-matter blocker means, when the medical practitioner performs such an examination. Even further, it provides such a system further comprising handed-deployment selector means for permitting selecting either right-handed or left-handed deployment of such bio-matter blocker means.

Even further, it provides such a system further comprising hand-holder means for permitting hand-holding of such bio-matter blocker means between such at least one portion of the patient and the face of the medical practitioner, when the medical practitioner performs such an examination. Even further, it provides such ay system further comprising hand-holder angled-deployer means for deploying such hand-holder means at least one angle relative to such viewer means. Even further, it provides such a system wherein such hand-holder angled-deployer means permits flat storage of such system. In accordance with another preferred embodiment hereof, this invention provides a system comprising each and every novel feature, element, combination, step and/or method disclosed or suggested by this patent application.

BRIEF DESCRIPTION OF THE DRAWINGS

FIG. 5 shows a perspective view of such contagion prevention system according to the preferred embodiment of FIG. 4.

FIG. 6 shows a plan view illustrating dimensions of such contagion prevention system according to the preferred embodiment of FIG. 6.

FIG. 7 shows a side view illustrating deployment of at least one thumb control tab of such contagion prevention system according to the preferred embodiment of FIG. 6.

FIG. 10A is a top plan view of another alternately preferred bio-matter shield of such contagion prevention system according to an alternately preferred embodiment of the present invention.

FIG. 10B is a partial top plan view further illustrating the bio-matter shield of FIG. 10A and an adhesive protector.

FIG. 10C is a perspective view of the bio-matter shield of FIG. 10A in position above a tongue depressor to install a shield middle flap.

FIGS. 10D, 10E, and 10F are perspective views further illustrating the preferred installation steps to install the illustrated preferred bio-matter shield.

DETAILED DESCRIPTION OF THE BEST MODES AND PREFERRED EMBODIMENTS OF THE INVENTION

Figure 1:
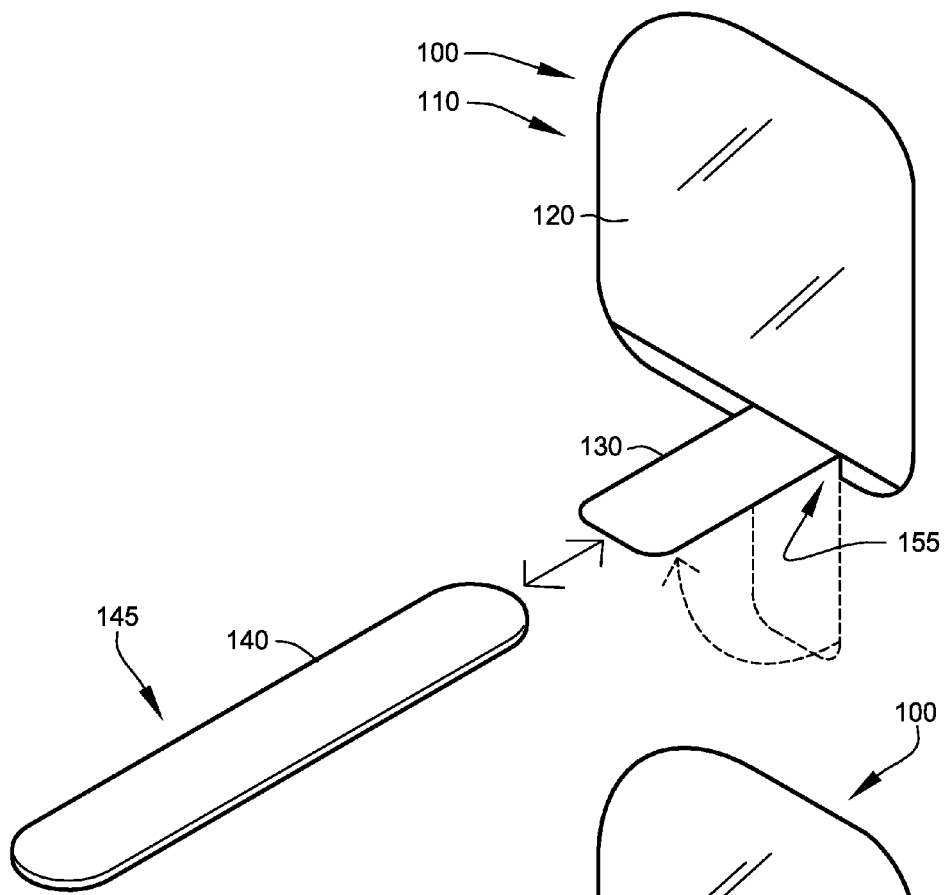
FIG. 1 shows a perspective view illustrating a contagion prevention system according to a preferred embodiment of the present invention.
Figure 2:
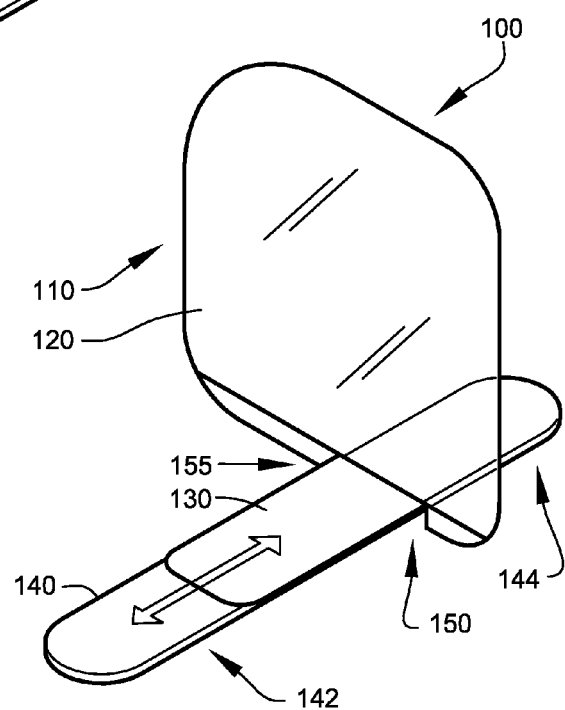
FIG. 2 shows a perspective view of such contagion prevention system, illustrating slide-adjustability of a contagion shield, according to the preferred embodiment of FIG. 1.

FIG. 1 shows a perspective view illustrating a contagion prevention system 100 according to a preferred embodiment of the present invention. FIG. 2 shows a perspective view of contagion prevention system 100, illustrating slide-adjustability of at least one bio-matter shield 110, according to the preferred embodiment of FIG. 1.

Contagion prevention system 100 preferably comprises bio-matter shield 110. Bio-matter shield 110 preferably is used in conjunction with at least one medical instrument 145, preferably at least one tongue depressor 140, as shown. Bio-matter shield 110 preferably may slide along the length of tongue depressor 140, as shown in FIG. 2, preferably to adjust the usable length of tongue depressor on a patient.

Figure 3:
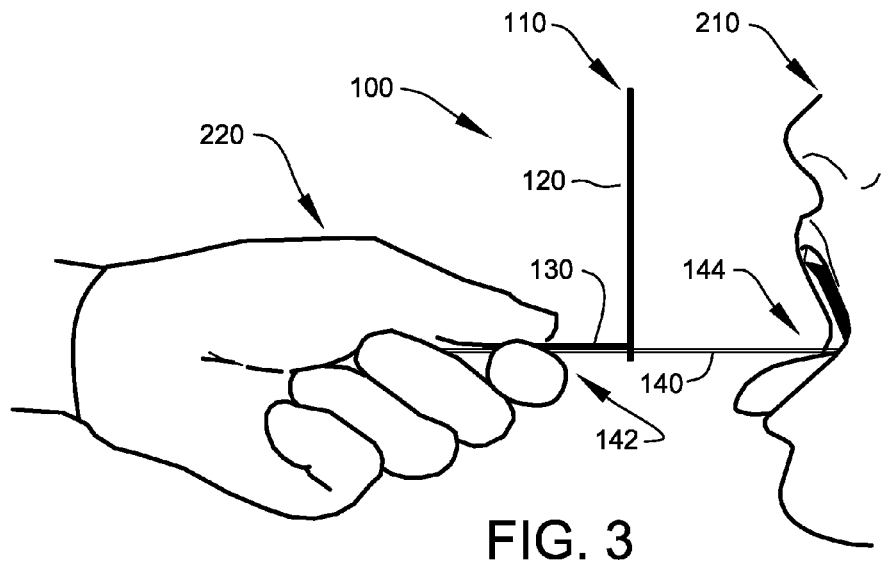
FIG. 3 shows a side view illustrating such contagion prevention system in use according to the preferred embodiment of FIG. 2.

Bio-matter shield 110 preferably comprises at least one medical device passage 155 (at least embodying herein at least one first medical-instrument passage structured and arranged to permit passage of at least one first medical instrument beyond said at least one bio-matter blocker; and at least embodying herein first medical-instrument passage means for permitting passage of at least one first medical instrument beyond said bio-matter blocker means), preferably allowing medical instrument 145 to be on both sides of bio-matter shield 110, as shown in FIG. 2. In effect, bio-matter shield 110 preferably intercedes between at least one handling end 142 of medical instrument 145 and at least one patient-interfacing end 144 of medical instrument 145, where handling end 142 is preferably designed to be held and manipulated by a hand and where patient-interfacing end 144 is preferably designed to interface with at least one patient 210, as shown in FIG. 3.

Medical device passage 155 preferably comprises at least one medical instrument guide, preferably at least one tongue depressor guide 150, as shown in FIG. 2. Tongue-depressor guide 150 preferably nests around tongue depressor 140 on three sides, as shown, preferably preventing bio-matter shield 110 from sliding off to one side (this arrangement at least herein embodying wherein said at least one first medical-instrument passage is capable of mating with such at least one tongue depressor; and at least herein embodying wherein said at least one first medical-instrument passage comprises at least one groove in said at least one bio-matter blocker). Tongue-depressor guide 150 (at least embodying herein wherein said at least one first medical-instrument passage is structured and arranged to permit passage of at least one tongue depressor beyond said at least one bio-matter blocker) preferably fits with tongue depressor 140, preferably assisting manipulation of bio-matter shield 110 and tongue depressor 140 as a single unit, during an examination. Upon reading the teachings of this specification, those skilled in the art will now appreciate that, under appropriate circumstances, considering such issues as future technologies, cost, future medical instruments, etc., other medical device passages, such as, for example, guide-slots, syringe-tip holes, other holes, other spaces situate adjacent to a bio-matter shield, etc., may suffice.

Bio-matter shield 110 preferably comprises at least one shield window 120 and at least one grip tab 130, as shown in FIG. 1. Grip tab 130 (at least embodying herein at least one hand-holder structured and arranged to permit hand-holding of said at least one bio-matter blocker between such at least one portion of the patient and the face of the medical practitioner, when the medical practitioner performs such an examination; and at least embodying herein hand-holder means for permitting hand-holding of said bio-matter blocker means between such at least one portion of the patient and the face of the medical practitioner, when the medical practitioner performs such an examination) preferably is gripped by a user 220 (see FIG. 3), such as a medical practitioner, with handling end 142 of medical instrument 145, which preferably allows single-hand manipulation of both medical instrument 145 and bio-matter shield 110, preferably unitarily, that is, a medical practitioner holds both medical instrument 145 and grip tab 130 of bio-matter shield 110 in a single hand (this arrangement at least embodying herein at least one unitary manipulator structured and arranged to permit unitary manipulation of said at least one bio-matter blocker together with such at least one first medical-instrument, when the medical practitioner performs such an examination; and at least embodying herein unitary manipulator means for permitting unitary manipulation of said bio-matter blocker means together with such at least one first medical-instrument, when the medical practitioner performs such an examination). Grip tab 130 preferably may be held against tongue depressor 140 with at least one finger or thumb, preferably preventing independent movement, by friction, of bio-matter shield 110 from tongue depressor 140. Since bio-matter shield is held in place relative to tongue depressor by the grip of user 220, loosening of the grip preferably allows independent adjustment of bio-matter shield 110 (at least embodying herein a cough shield capable of being held together with a tongue depressor by a single hand in a configuration usable during oral examination of a patient to assist preventing spattering of oral fluids of the patient on an examining medical practitioner; and at least embodying herein at least one bio-matter blocker structured and arranged to assist blocking of bio-matter, potentially bearing contagion, expelled from the patient toward the face of the medical practitioner when the medical practitioner performs an examination requiring close proximity to the patient; and at least embodying herein bio-matter blocker means for assisting blocking of bio-matter, potentially bearing contagion, expelled from the patient toward the face of the medical practitioner, when the medical practitioner performs an examination requiring close proximity to the patient) relative to tongue depressor 140 (this arrangement at least embodying herein at least one relative-position adjuster structured and arranged to permit adjustment of such at least one first medical-instrument relative in position to said at least one bio-matter blocker, when the medical practitioner performs such an examination; and at least embodying herein relative-position adjuster means for permitting adjustment of such at least one first medical-instrument relative in position to said bio-matter blocker means, when the medical practitioner performs such an examination). Shield window 120 (at least embodying herein at least one viewer structured and arranged to permit viewing of at least one portion of the patient through said at least one bio-matter blocker, when the medical practitioner performs such an examination requiring close proximity to the patient; and at least embodying herein viewer means for permitting viewing of at least one portion of the patient through said bio-matter blocker means, when the medical practitioner performs such an examination requiring close proximity to the patient) preferably comprises at least one transparent barrier, as shown (this arrangement at least embodying herein allowing viewing through said cough shield).

In use, a medical practitioner holds both medical instrument 145 and grip tab 130 of bio-matter shield 110 in a single hand. Then for an examination of the patient, requiring close proximity (i.e., the medical practitioner must be within an arm's reach of the patient), the medical practitioner looks through shield window 120, preferably at a portion of the patient (such as the interior of the mouth or throat), while utilizing patient-interfacing end 144 with patient (i.e. using the end of a tongue depressor to depress the patient's tongue). In effect, this unitary manipulation frees the other hand of the medical practitioner for using other medical instrument 145.

Figure 4:
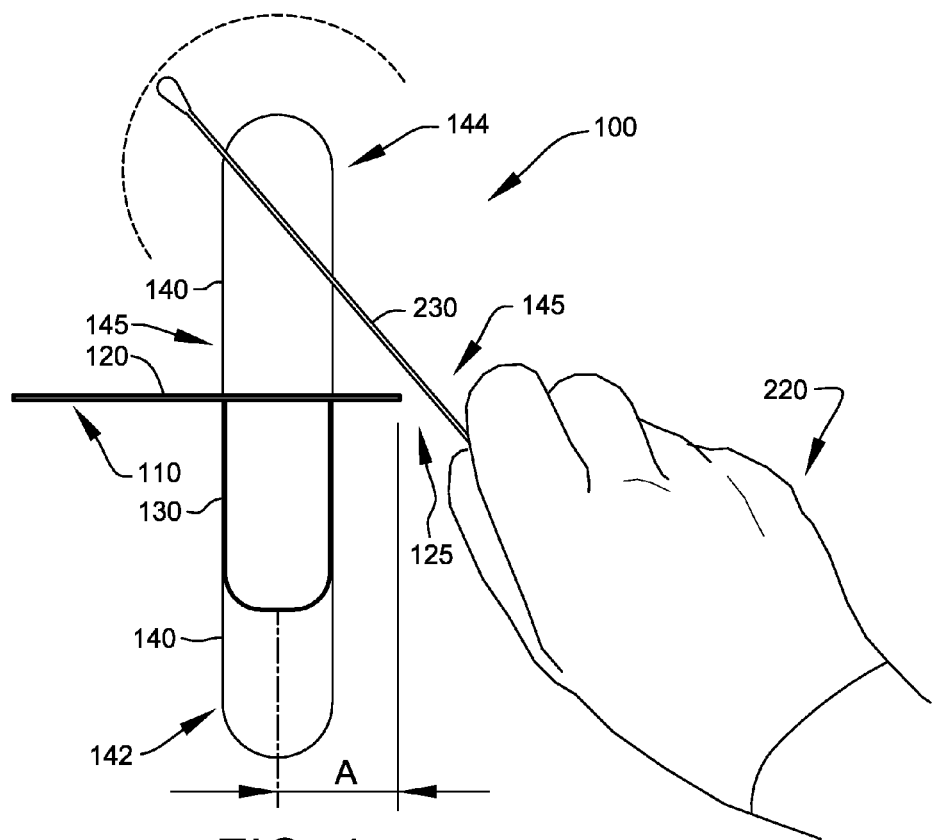
FIG. 4 shows a top view of such contagion prevention system, illustrating reach of culture swab around the contagion shield, according to the preferred embodiment of FIG. 3.

FIG. 3 shows a side view illustrating contagion prevention system 100 in use according to the preferred embodiment of FIG. 2. FIG. 4 shows a top view of contagion prevention system 100, illustrating reach of at least one culture swab 230 around bio-matter shield 110, according to the preferred embodiment of FIG. 3.

Shield window 120 preferably allows user 220 to see through to the oral cavity of a patient 210, as shown. Shield window 120 preferably also places a fluid barrier between patient 210 and user 220, preferably preventing potential direct contagion from bio-matter which may be expelled by patient 210 from coughing, breathing, etc. (this arrangement at least herein embodying wherein potential spread of contagion from the patient to the medical practitioner is prevented, while the medical practitioner performs such an examination requiring close proximity to the patient). Bio-matter (biological matter) refers to any substance derived from biological functions or comprising cells from a biological organism, such as, for example, saliva, phlegm, mucus, blood, oral aerosol, pus, sputum, etc.

In addition, shield window 120 is preferably asymmetrically aligned with grip tab 130 (and thereby tongue depressor 140). Shield window 120 preferably comprises, through this asymmetric disposition, at least one peripheral passage 125 (this arrangement at least embodying herein allowing use of another medical instrument in a second hand without displacing such configuration which assists preventing spattering of oral fluids of the patient on an examining medical practitioner), preferably allowing insertion of at least one second medical instrument 145, depicted in FIG. 4 as culture swab 230, preferably through peripheral passage 125 on one side of shield window 120 (this arrangement at least herein embodying wherein said at least one second medical-instrument passage is structured and arranged to permit passage of at least one culture swab beyond said at least one bio-matter blocker). Peripheral passage 125 preferably allows culture swab 230 free range of motion to reach any area of the oral cavity of patient 210, as shown in FIG. 4 (this arrangement at least embodying herein at least one independent manipulator structured and arranged to permit manipulation of such at least one second medical-instrument independent from said at least one bio-matter blocker, when the medical practitioner performs such an examination; and at least embodying herein independent manipulator means for permitting manipulation of such at least one second medical-instrument independent from said bio-matter blocker means, when the medical practitioner performs such an examination). Upon reading the teachings of this specification, those skilled in the art will now appreciate that, under appropriate circumstances, considering such issues as future technologies, advances in medical practices, etc., other medical instruments, such as, for example, syringes, suction devices, endoscopes, etc., may suffice.

In use for oral examinations, the medical practitioner is able to maintain bio-matter shield 110 interceding between their face and the oral cavity of the patient, preferably blocking bio-matter expelled by patient by coughing, breathing, etc. from reaching the face of the medical practitioner (during examination). Additionally medical practitioner may handle multiple medical instruments 145, given in the preferred embodiments described herein as tongue depressor 140 and culture swab 230. Further, should medical practitioner need to adjust their viewing angle, bio-matter shield 110 may preferably be manipulated in conjunction with tongue depressor 140, to maintain the position of bio-matter shield 110 relative to the patient and the medical practitioner, as described, without having to set down one of medical instruments 145.

FIG. 5 shows a perspective view of bio-matter shield 110 according to the preferred embodiment of FIG. 4. FIG. 6 shows a plan view illustrating dimensions of bio-matter shield 110 according to the preferred embodiment of FIG. 6. FIG. 7 shows a side view illustrating deployment of grip tab 130 of bio-matter shield 110 according to the preferred embodiment of FIG. 6.

Bio-matter shield 110 preferably is stored flat, having shield window 120 and grip tab 130 preferably aligned to fall within the same plane, as shown in FIG. 5 (this arrangement at least herein embodying wherein said at least one hand-holder angled-deployer permits flat storage of said system; and this arrangement at least herein embodying wherein said hand-holder angled-deployer means permits flat storage of said system). Bio-matter shield 110 preferably further comprises at least one folding hinge 132, preferably between grip tab 130 and shield window 120. Folding hinge 132 preferably permits angling (or folding) grip tab 130 with respect to shield window 120. Folding hinge 132 preferably is stiff, preferably allowing folding hinge to maintain, after folding, the angle between grip tab 130 and shield window 120. Folding hinge 132 preferably comprises at least one folding score 134, preferably to direct folding at folding hinge 132 and preferably prevent accidental folding along grip tab 130 and prevent folding in shield window 120. In use, folding hinge 132 (at least embodying herein at least one hand-holder angled-deployer structured and arranged to deploy said at least one hand-holder at at least one angle relative to said at least one viewer; and at least embodying herein hand-holder angled-deployer means for deploying said hand-holder means at at least one angle relative to said viewer means) is folded to angle grip tab 130 at an appropriate angle for holding grip tab 130 and deploying shield window 120 between user 220 and patient 210. When in use with tongue depressor 140, grip tab 130 preferably folds out at folding hinge 132 to about 90 degrees from shield window 120, as shown in FIG. 7. Upon reading the teachings of this specification, those skilled in the art will now appreciate that, under appropriate circumstances, considering such issues as future medical practices, medical practitioner viewing preferences, etc., other angles, may suffice. Upon reading the teachings of this specification, those skilled in the art will now appreciate that, under appropriate circumstances, considering such issues as cost, future medical practices, future technology, etc., other shield holding methods, such as, for example, individually without a medical instrument, holding with other medical devices, etc., may suffice.

Grip tab 130 preferably may be folded in either direction, preferably deploying for use in either a right-handed or left-handed configuration, preferably positioning peripheral passage 125 on the right or left, respectively, of shield window 120. Preferably, grip tab 130 thereby positions the asymmetry of shield window 120 toward the right or the left of tongue depressor 140. This arrangement at least embodies herein a configuration selector allowing selection between left-handed and right-handed use; and this arrangement at least embodies herein at least one handed-deployment selector structured and arranged to permit selecting either right-handed or left-handed deployment of said at least one bio-matter blocker; and this arrangement at least embodying herein handed-deployment selector means for permitting selecting either right-handed or left-handed deployment of said bio-matter blocker means.

Shield window 120 preferably comprises a height B of about 7¼ cm. Shield window 120 preferably comprises a width of about 7¼ cm, preferably disposed as width E (long side from edge of shield window 120 to grip tab 130) of about 4 cm, width F (of grip tab 130) of about 2 cm, and width G (short side from grip tab 130 to edge of shield window 120) of about 1¼ cm, as shown in FIG. 6. Grip tab 130 preferably comprises a length C of about 4 cm, as shown. Upon reading the teachings of this specification, those skilled in the art will now appreciate that, under appropriate circumstances, considering such issues as average patient size, cost, available materials, etc., other dimensions, such as, for example, wider, taller, shorter, narrower, etc., may suffice.

Tongue depressor guide 150 preferably comprises a depth D of about ½ cm recessed into shield windows 120 from bottom edge of shield window 120 to fold line of grip tab 130, as shown. Therefore, the asymmetry of shield window 120 may be measured on the short side (comprising peripheral passage 125), as shown in FIG. 4, preferably comprising width A (from centerline of grip tab 130 to edge of shield window 120) of about 2¼ cm. Upon reading the teachings of this specification, those skilled in the art will now appreciate that, under appropriate circumstances, considering such issues as cost, future technologies, etc., other peripheral passages, such as, for example, holes, cutouts, instrument-permeable membranes, etc., may suffice.

Shield window 120 preferably comprises rounded corners, preferably comprising radius H of about 1 cm, and preferably radius I of about 3 cm. Upon reading the teachings of this specification, those skilled in the art will now appreciate that, under appropriate circumstances, considering such issues as cost, materials, etc., other corner geometries, such as, for example, squared, angled, other radii, etc., may suffice.

Figure 8:
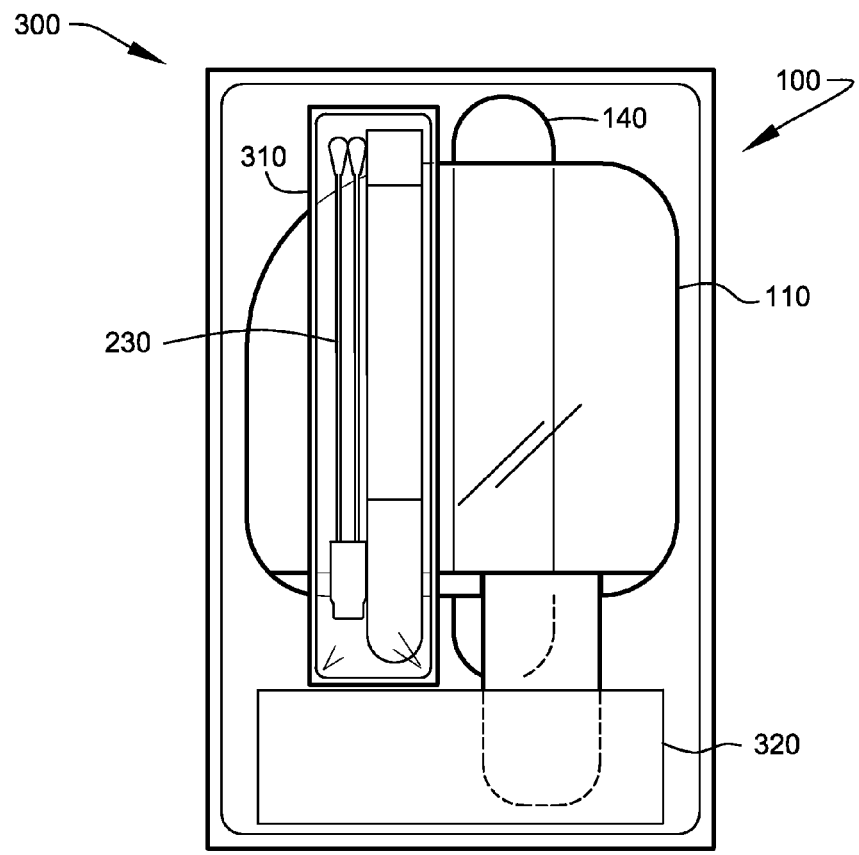
FIG. 8 shows a diagrammatic view of such contagion prevention system, illustrating at least one examination kit containing a contagion shield, according to the preferred embodiment of FIG. 7.

FIG. 8 shows a diagrammatic view of contagion prevention system 100, illustrating at least one examination kit 300 containing bio-matter shield 110, according to the preferred embodiment of FIG. 7. Examination kit 300 preferably comprises bio-matter shield 110 (at least embodying herein providing at least one bio-matter blocker structured and arranged to assist blocking of bio-matter, potentially bearing contagion, expelled from the patient toward the face of the medical practitioner), tongue depressor 140, and at least one culture swab kit 310 (preferably containing a plurality of culture swabs 230). Examination kit 300 preferably is contained in at least one blister pack, preferably as a sterile environment. Examination kit 300 preferably further comprises instructions 320 (at least embodying herein instructing use of bio-matter blocker in conjunction with at least one tongue depressor), preferably instructing in the use and deployment of bio-matter shield 110 with respect to tongue depressor 140 and preferably additionally culture swab 230 of culture swab kit 310.

Figure 9:
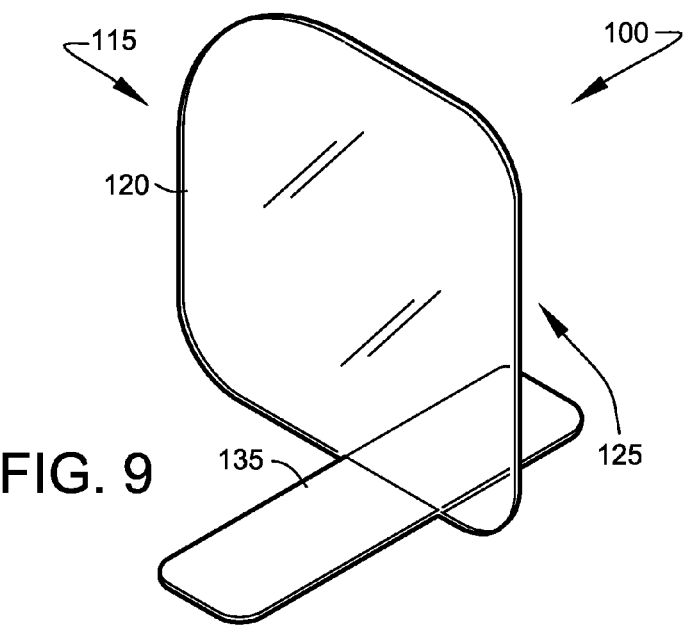
FIG. 9 shows a perspective view illustrating an alternately preferred bio-matter shield of such contagion prevention system according to an alternately preferred embodiment of the present invention.

FIG. 9 shows a perspective view illustrating an alternately preferred bio-matter shield 115 of contagion prevention system 100 according to an alternately preferred embodiment of the present invention. While many of the features of bio-matter shield 115 are retained from bio-matter shield 110, instead of grip tab 130 of bio-matter shield 110, bio-matter shield 115 preferably comprises at least one grip tab 135.

Grip tab 135 preferably comprises at least one fixed position relative to shield window 120. Shield window 120 is preferably mounted at a fixed angle of about 90 degrees on grip tab 135. Grip tab 135 operationally functions similar to grip tab 130 during use, however grip tab 135 is preferably permanently deployed in both left-handed and right-handed configurations. Bio-matter shield 115 preferably is rotated 180 degrees with respect to tongue depressor 140 to change between left-handed and right-handed configurations, preferably, preferably positioning peripheral passage 125 (at least embodying herein at least one second medical-instrument passage structured and arranged to permit passage of at least one second medical instrument beyond said at least one bio-matter blocker; and at least embodying herein second medical-instrument passage means for permitting passage of at least one second medical instrument beyond said bio-matter blocker means) on the left or right, respectively, of shield window 120.

FIG. 10A is a top plan view of another alternately preferred bio-matter shield 502 of contagion prevention system 100 according to an alternately preferred embodiment of the present invention. Bio-matter shield 502 preferably mounts on tongue depressor 140 and is preferably made of a transparent material, preferably plastic. Shape of bio-matter shield 502 is preferably as shown for reasons that will become apparent. As shown, adhesive 503 is placed on middle attachment flap 506, first side attachment flap 507, and second side attachment flap 508.

FIG. 10B is a partial top plan view further illustrating bio-matter shield 502 of FIG. 10A and an adhesive protector 504 (shield) sized to fit over and protect areas of adhesive 503. Protector 504 preferably comprises at least one pull tab 505, preferably for ease of protector 504 removal when a user wishes to use the adhesive-coated areas.

FIG. 10C is a perspective view of the bio-matter shield 502 of FIG. 10A in position (areas of adhesive 503 pointing downward) above a tongue depressor 140, to install a shield middle attachment flap 506. After removal of protector 504, shield middle attachment flap 506 is preferably pressed downward onto an area 527 (shown in dotted lines) roughly in the middle of tongue depressor 140 so that shield middle attachment flap 506 adheres to tongue depressor 140.

FIGS. 10D, 10E, and 10F are perspective views further illustrating the preferred installation steps to install the illustrated preferred bio-matter shield 502. After shield middle attachment flap 506 has been adhered, first side attachment flap 507 is pressed on top of shield middle attachment flap 506 to adhere it; and then second side attachment flap 508 is similarly pulled over into place above the previously adhered elements (shield middle attachment flap 506 and first side attachment flap 507) and pressed down to adhere second side attachment flap 508 to first side attachment flap 507, as shown in the resulting configuration detail of FIG. 10F.

Figures 10G, 10H:
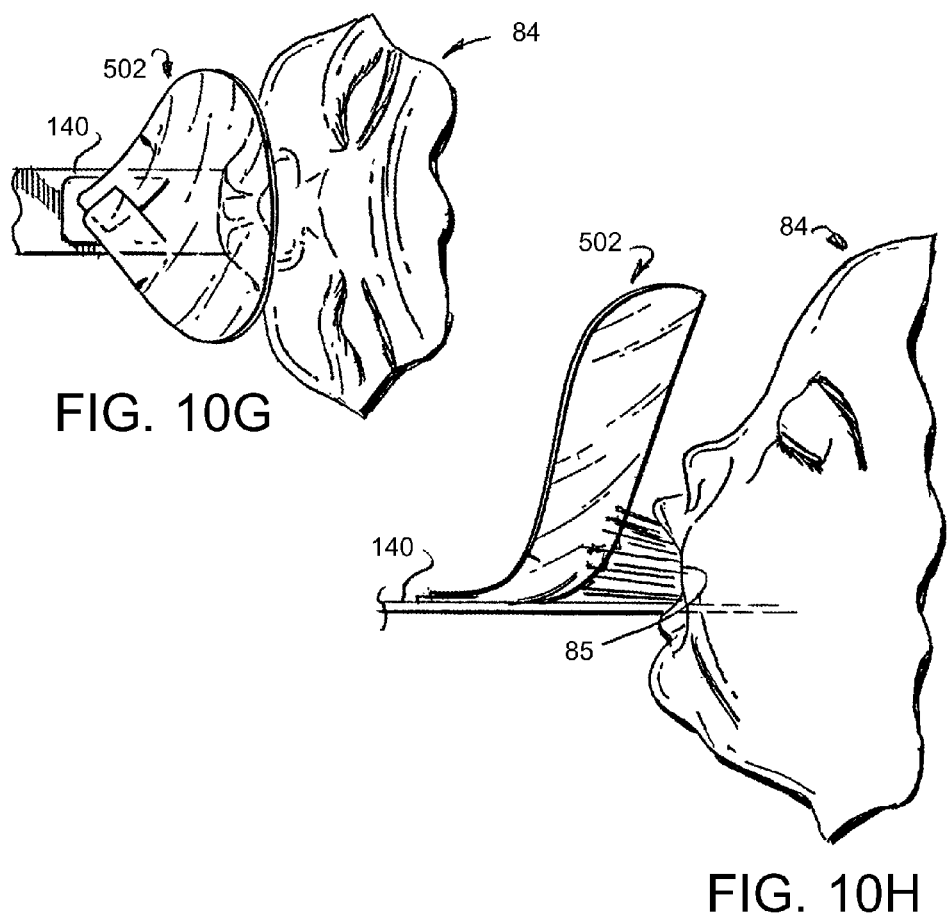
FIG. 10G is a top plan view of the illustrated preferred bio-matter shield in pediatric use.
FIG. 10H is a side elevation view of the illustrated preferred bio-matter shield in pediatric use.

FIG. 10G is a top plan view of the illustrated preferred bio-matter shield 502 in pediatric use. It is seen that mouth 85 of child 84 is shielded from the physician using tongue depressor 140 by the intervention of bio-matter shield 502 mounted on tongue depressor 140. FIG. 10H is a side elevation view of the illustrated preferred bio-matter shield 502 in pediatric use. FIG. 10H illustrates how the position of bio-matter shield 502 on depressor 140 effectively stops germs and debris emanating from mouth 85 during a cough.

Upon reading the teachings of this specification, those skilled in the art will now appreciate that, under appropriate circumstances, considering such issues as cost, future technologies, future bio-matter shielding needs, etc., other uses of bio-matter shields, such as, for example, shielding back-spray of syringes, shielding otoscopes during examinations, etc., may suffice. By way of example, it is noted that such a transparent shield as described could be used in combination with other medical devices such as a syringe to provide similar cough protection as during a tonsillar aspiration. The same device can also be attached on a syringe to provide other functions such as irrigation spray protection as a wound is infiltrated under pressure, with the flexible plastic shield forming alternatively a concave or convex shield depending on the positioning to which the shield is bent.

The same device of the cough shield, as above noted, could also be used to attach to another component such as a syringe for the purpose of acting as an infiltration splash shield. One usually infiltrates a wound with a needle and syringe correctly by removing the needle while simultaneously using a high pressure counteracting force to infuse the medication, such as a local anesthetic into a wound. And it is the common safer practice to inject medication after a needle is inserted into the skin; then the syringe plunger is pulled back to create a negative pressure to make sure that one does not withdraw blood; this would indicate that one is undesirably in a blood vessel rather than in the desired location of being in the upper-layers skin tissue itself where the nerve endings are located. After such determination is made that one is not in the blood vessel, one then forces the medication through the needle into the skin while withdrawing the needle. This requires the use of a high pressure to infiltrate the closed space of the skin with the infused medication, requiring greater attention to the force being instilled and the forward pressure of the syringe and the counteracting withdrawing forces of pulling out the needle. In addition, as a great force is often required, the hand-held system is often less stable. As the needle is being removed, the position of the open tip portion of the needle position cannot be reliably visualized as it is under the skin. Often, as the needle is fully withdrawn from the skin, the continuing high pressured medication continues and sprays the medication into a patient's bloody wound, displacing not only the medication in an uncontrolled spray-like fashion, but also the patient's bodily fluid. This creates a health hazard to medical personnel as well as increasing cleanup time and soiling hospital equipment and patient clothing. Some medical personnel put on costly, cumbersome and time-consuming face masks with shields and gowns for protection during such a procedure. Others place their hand over the site which obstructs the sight and places their hand in close proximity to the potentially hazardous free end of the injecting needle. Having a simple inexpensive shield that could work in combination with such a syringe and needle system would be desirable. Having a device system that could also attach to other devices for other protective functions such as attaching to a tongue depressor to act as a cough shield would provide more versatility and increase the potential marketability and success of the device. Having a device with a means of attachment to another device would eliminate the number of hands and operators necessary to achieve the desired function or procedure. Having such a device with an easy simple attachment would speed the completion of the procedure as would desirable in a busy doctor's office. Having such a device that is easy to use and inexpensive to manufacture and therefore to sell would increase the use of the device and therefore reduce the potential contamination of hospital personnel from patients. Having a transparent material would allow visualization through the shield. Having a flexible material might allow for a nonplanar attachment of an otherwise flat material. Having an attachment of flexible material on a convex surface would increase the rigidity of the material and would stabilize other portions of the material bent in a concave fashion. Having a stable material bent in a concave fashion would permit a relative narrow attachment surface to accommodate a relatively larger concave bent surface to act as a splash shield. By varying the position of the bend, one could vary the angle and position of the shield. Such a large bent splash shield would protect the operator behind the shield and would not interfere with the forward advancement of the needle. Since the shield must extend beyond the syringe and preferably cover a large area, having a bent shield would facilitate such an operation without the shield edge obstructing the advancement of the needle tip below. Such a shield could be made of an inexpensive flat flexible material with at least one attachment means and could be used for other functions as well, such as a cough shield on a tongue depressor. Such a preferred shield would be relatively simple, inexpensive to manufacture, increasing the marketability and usage of the device for its desired advantages. The same principles described above could be related to other components and procedures such as wound irrigation without a needle.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A system, relating to preventing transmission of contagion from a patient to a medical practitioner, said system comprising:
   a) at least one bio-matter blocker structured and arranged to assist blocking of bio-matter, potentially bearing contagion, expelled from the patient toward the face of the medical practitioner when the medical practitioner performs an examination requiring close proximity to the patient;
   b) at least one viewer structured and arranged to permit viewing of at least one portion of the patient through said at least one bio-matter blocker, when the medical practitioner performs such an examination requiring close proximity to the patient;
   c) at least one first medical-instrument passage structured and arranged to permit passage of at least one first medical instrument beyond said at least one bio-matter blocker;
   d) at least one unitary manipulator structured and arranged to permit unitary manipulation of said at least one bio-matter blocker together with such at least one first medical-instrument, when the medical practitioner performs such an examination; and
   e) at least one relative-position adjuster structured and arranged to permit adjustment of such at least one first medical-instrument relative in position to said at least one bio-matter blocker, when the medical practitioner performs such an examination;
   f) wherein potential spread of contagion from the patient to the medical practitioner is prevented, while the medical practitioner performs such an examination requiring close proximity to the patient;
   g) wherein said at least one first medical-instrument passage is structured and arranged to permit passage of at least one tongue depressor beyond said at least one bio-matter blocker;
   h) wherein said at least one first medical-instrument passage is capable of mating with such at least one tongue depressor;
   i) wherein said at least one first medical-instrument passage comprises at least one groove in said at least one bio-matter blocker.

2. The system according to claim 1 further comprising at least one hand-holder structured and arranged to permit hand-holding of said at least one bio-matter blocker between such at least one portion of the patient and the face of the medical practitioner, when the medical practitioner performs such an examination.

3. The system according to claim 1 further comprising at least one handed-deployment selector structured and arranged to permit selecting either right-handed or left-handed deployment of said at least one bio-matter blocker.

4. The system according to claim 1 further comprising at least one second medical-instrument passage structured and arranged to permit passage of at least one second medical instrument beyond said at least one bio-matter blocker.

5. The system according to claim 4 wherein said at least one first medical-instrument passage is structured and arranged to permit passage of at least one tongue depressor beyond said at least one bio-matter blocker.

6. The system according to claim 5 wherein said at least one second medical-instrument passage is structured and arranged to permit passage of at least one culture swab beyond said at least one bio-matter blocker.

7. The system according to claim 4 further comprising at least one independent manipulator structured and arranged to permit manipulation of such at least one second medical-instrument independent from said at least one bio-matter blocker, when the medical practitioner performs such an examination.

8. The system according to claim 7 further comprising at least one hand-holder structured and arranged to permit hand-holding of said at least one bio-matter blocker between such at least one portion of the patient and the face of the medical practitioner, when the medical practitioner performs such an examination.

9. The system according to claim 7 further comprising at least one handed-deployment selector structured and arranged to permit selecting either right-handed or left-handed deployment of said at least one bio-matter blocker.

10. The system according to claim 1 further comprising at least one hand-holder angled-deployer structured and arranged to deploy said at least one hand-holder at at least one angle relative to said at least one viewer.

11. The system according to claim 10 wherein said at least one hand-holder angled-deployer permits flat storage of said system.

* * * * *